United States Patent
Yi et al.

(10) Patent No.: US 11,298,678 B2
(45) Date of Patent: Apr. 12, 2022

(54) FABRICATION OF MACROPOROUS POLYMERIC HYDROGEL MICROPARTICLES

(71) Applicant: Trustees of Tufts College, Medford, MA (US)

(72) Inventors: Hyunmin Yi, Lexington, MA (US); Eunae Kang, Medford, MA (US); Sukwon Jung, Incheon (KR); John H. Abel, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 286 days.

(21) Appl. No.: 16/090,453

(22) PCT Filed: Mar. 22, 2017

(86) PCT No.: PCT/US2017/023545
§ 371 (c)(1),
(2) Date: Oct. 1, 2018

(87) PCT Pub. No.: WO2017/172437
PCT Pub. Date: Oct. 5, 2017

(65) Prior Publication Data
US 2019/0111412 A1    Apr. 18, 2019

Related U.S. Application Data

(60) Provisional application No. 62/315,349, filed on Mar. 30, 2016.

(51) Int. Cl.
| | |
|---|---|
| *B01J 20/26* | (2006.01) |
| *B01J 20/24* | (2006.01) |
| *B01J 20/28* | (2006.01) |
| *B01J 20/30* | (2006.01) |
| *A61K 47/69* | (2017.01) |
| *A61K 47/58* | (2017.01) |
| *C08L 5/08* | (2006.01) |
| *C08J 3/075* | (2006.01) |

(52) U.S. Cl.
CPC ............ *B01J 20/261* (2013.01); *A61K 47/58* (2017.08); *A61K 47/6927* (2017.08); *B01J 20/24* (2013.01); *B01J 20/2808* (2013.01); *B01J 20/28047* (2013.01); *B01J 20/28083* (2013.01); *B01J 20/28085* (2013.01); *B01J 20/3007* (2013.01); *B01J 20/3064* (2013.01); *B01J 20/3071* (2013.01); *B01J 20/3085* (2013.01); *C08J 3/075* (2013.01); *C08L 5/08* (2013.01); *C08J 2333/26* (2013.01); *C08J 2405/08* (2013.01)

(58) Field of Classification Search
None
See application file for complete search history.

(56) References Cited

U.S. PATENT DOCUMENTS

| | | | |
|---|---|---|---|
| 4,587,018 A | 5/1986 | Blomback et al. | |
| 5,599,916 A | 2/1997 | Dutkiewicz et al. | |
| 7,758,919 B2 | 7/2010 | Ozin et al. | |
| 2006/0210710 A1* | 9/2006 | Buiser | C08J 3/12 427/212 |
| 2010/0291055 A1* | 11/2010 | Athanasiadis | A61L 31/041 424/94.1 |
| 2010/0330645 A1 | 12/2010 | Defrees et al. | |
| 2011/0104052 A1* | 5/2011 | Barnett | A61K 9/1617 424/1.21 |
| 2012/0058355 A1 | 3/2012 | Lee et al. | |
| 2014/0370500 A1* | 12/2014 | Ghanavi | A61K 9/5161 435/6.1 |
| 2015/0114580 A1 | 4/2015 | McKee et al. | |
| 2016/0319059 A1 | 11/2016 | Vlasov et al. | |

FOREIGN PATENT DOCUMENTS

| | | |
|---|---|---|
| WO | WO-1996/020698 A2 | 7/1996 |
| WO | WO-2003/072616 A1 | 9/2003 |
| WO | WO-2008/137910 A2 | 11/2008 |
| WO | WO-2011/057131 A1 | 5/2011 |
| WO | WO-2015/154082 A1 | 10/2015 |

OTHER PUBLICATIONS

International Search Report and Written Opinion for International Application No. PCT/US2017/23545 dated Jun. 22, 2017.
International Preliminary Report on Patentability for International Application No. PCT/US2017/23545 dated Oct. 2, 2018.
Helgeson et al "Hydrogel Microparticles from Lithographic Processes: Novel Materials for Fundamental and Applied Colloid Science" Current Opinion in Colloid and Interface Science vol. 16, pp. 106-117, 2011.
Lee et al "Development of Macroporous Poly(Ethylene Glycol) Hydrogel Arrays Within Microfluidic Channels" Biomacromolecules vol. 11, pp. 3316-3324, 2010.
Liu et al "Tough and Highly Stretchable Polyacrylamide Nanocomposite Hydrogels with Chitin Nanocrystals" International Journal of Biological Macromolecules vol. 78, pp. 23-31, 2015.
Shen et al. "Hydrogels Based on Cellulose and Chitin: Fabrication, Properties, and Applications" Green Chemistry vol. 18, pp. 53-75, 2016.
Usablestats "Fundamentals of Statistics 1: Basic Concepts: The Standard Deviation and Coefficient of Variation" usablestats.com/lessons/sdcv, p. 2, 2014.

* cited by examiner

*Primary Examiner* — Ronak C Patel
(74) *Attorney, Agent, or Firm* — Foley Hoag LLP; Dana M. Gordon; Laura A. Wzorek

(57) ABSTRACT

A polymeric hydrogel microparticle that contains polyacrylamide and chitosan, the chitosan uniformly incorporated in a polyacrylamide matrix. The microparticle, having a coefficient variation of 0 to 2% and containing macropores with an average size of 1 to 60 nm, is capable of transporting biomolecules conjugated to it. Also disclosed are a method of fabricating such a microparticle in a micromold via photo-induced radical polymerization and a one-pot method of conjugating biomolecules to polymeric hydrogel microparticles.

12 Claims, No Drawings

FABRICATION OF MACROPOROUS POLYMERIC HYDROGEL MICROPARTICLES

CROSS-REFERENCE TO RELATED APPLICATIONS

This application is the National Stage of International Application No. PCT/US2017/023545, filed Mar. 22, 2017, which claims the benefit of Provisional Application No. 62/315,349, filed Mar. 30, 2016. The contents of both applications are hereby incorporated by reference in their entirety.

BACKGROUND

Polymeric hydrogel microparticles containing polymer networks are capable of transporting biomolecules, e.g., proteins, via conjugation of the biomolecules with the polymeric networks. They have gained increased attention in various biomedical applications, e.g., medical diagnostics, bio-sensing, and biological threat detection.

To achieve desired performance for specific needs, polymeric hydrogel microparticles can be fabricated by using different methods to control their structures such as morphology and mesh size.

When fabricated via batch processes using dispersion or emulsion polymerization, the polymeric hydrogel microparticles thus prepared are generally polydisperse, i.e., non-uniform.

On the other hand, microfluidics-based techniques have been utilized to fabricate highly uniform hydrogel microparticles. Yet, this approach, requiring complex devices, is not scalable to produce microparticles with macroporous structures for rapid biomolecule conjugation.

Various porogens have been used to fabricate hydrogel microparticles. However, using them often leads to non-uniform network structures and compromised mechanical integrity.

There is a need to develop facile fabrication of desirable macroporous polymeric hydrogel microparticles.

SUMMARY

The present invention relates to a process of preparing polymeric hydrogel microparticles containing macropores. The process allows for unexpectedly facile fabrication of highly uniform polymeric hydrogel microparticles with controlled macroporous structures. Moreover, the polymeric hydrogel microparticles thusly prepared exhibit unexpectedly rapid biomolecule conjugation.

In one aspect, this invention is a method of fabricating a polymeric hydrogel microparticle. The method includes four steps: (1) providing an aqueous pre-polymer solution containing acrylamide, bisacrylamide, chitosan, and a photoinitiator, in which the chitosan has an average molar mass of 4,500-200,000 Da (e.g., 5,000 Da); (2) filling a 2D shaped poly-dimethylsiloxane (PDMS) micromold with the aqueous pre-polymer solution; (3) inducing radical polymerization by exposing the aqueous pre-polymer solution to UV light for 0.25 to 1 hour to produce a 2D shape-encoded polymeric hydrogel microparticle formed of polyacrylamide and chitosan; and (4) collecting the microparticle thus formed. Among these steps, steps (1)-(3) are preferably conducted in a humid chamber with a humidity of 90-98% (e.g., 92%).

The aqueous pre-polymer solution can have an acrylamide/bisacrylamide ratio of 4:1 to 100:1 (e.g., 29:1). Typically, it contains a poly(ethylene glycol) porogen that has a molecular weight of 200 to 20,000 Da (e.g., 8,000 Da) and a content of 1-4 w/v %.

The PDMS micromold used in the above method can have various 2D shapes, e.g., hexagon, triangle, square, disk, pentagon, or cross.

This method can further include a rinsing step, i.e., washing the collected microparticle with a saline sodium citrate buffer solution.

Another aspect of this invention is a macroporous polymeric hydrogel microparticle that can be prepared by the above-described method.

In one embodiment, the macroporous polymeric hydrogel microparticle has a total polymer content of 5 to 50 w/v % (e.g., 15 w/v %) and is capable of conjugating to a biomolecule, e.g., a DNA or a protein, that has a molecular weight greater than 200,000 Da.

Still another aspect of this invention is a polymeric hydrogel microparticle that contains polyacrylamide and chitosan. The microparticle has a coefficient variation of 0 to 2% (e.g., 1%) and contains macropores having an average size of 1 to 60 nm (e.g., 11 to 60 nm). The chitosan in the microparticle, uniformly incorporated in a polyacrylamide matrix, typically has an average molar mass of 4,500-200,000 Da (e.g., 5,000 Da). It contains primary amines having a pKa value of 6.0-6.9 (e.g., 6.5), which are capable of conjugating to biomolecules via an acyl or nucleophilic substitution reaction.

Still within the scope of this invention is a one-pot method of conjugating biomolecules with polymeric hydrogel microparticles. The method includes first both modifying two or more biomolecules with two or more anchors and activating two or more 2D shape-encoded polymeric hydrogel microparticles with two or more activators, and then mixing the modified biomolecules and the activated polymeric hydrogel microparticles in one pot to conjugate each of the biomolecules with one of the microparticles, thereby producing different biomolecule-microparticle conjugates.

Each of the activators contains a tetrazine (Tz) group or an alkyne group, and each of the anchors contains a trans-cyclooctene (TCO) group or an azide group.

The polymeric hydrogel microparticles can be fabricated in the presence of a poly(ethylene glycol) porogen that has a molecular weight of 200 to 20,000 Da (e.g., 8,000 Da) and a content of 1-4 w/v %.

Examples of the biomolecules include, but are not limited to, single-stranded DNA and fluorescent protein R-phycoerythrin. These biomolecules can be conjugated with polymeric hydrogel microparticles via a strain-promoted alkyne-azide cycloaddition reaction or a Tz-TCO ligation reaction.

The details of the invention are set forth in the description below. Other features, objects, and advantages of the invention will be apparent from the following detailed description of several embodiments, and also from the appending claims.

DETAILED DESCRIPTION

Disclosed first in detail herein is a method of preparing macroporous polymeric hydrogel microparticles in a micromold by photo-induced radical polymerization.

Initially, a 2D-shaped, e.g., hexagon-shaped, polydimethylsiloxane (PDMS) micromold is obtained via thermal curing of elastomer on a photolithographically patterned silicon master mold, e.g., a PDMS micromold including hexagon-shaped microwells.

An aqueous pre-polymer solution is subsequently prepared by mixing chitosan (CS), acrylamide (AAm), bisacrylamide (Bis), and photoinitiator (PI) in water. To impart chemical functionality for facile biofunctionalization, e.g., biomolecule conjugation, one can include in the pre-polymer solution an amino-polysaccharide chitosan that contains abundant primary amines with a unique $pK_a$ value of 6.0-6.9 (e.g., 6.5). The chitosan typically has an average molar mass of 4,500-200,000 Da (e.g., 4,500-100,000 Da and 4,500-10,000 Da).

The pre-polymer solution is filled into each of the microwells of the PDMS micromold by rubbing the micromold with a disposable pipet tip.

The above procedures are preferably conducted at a relative humidity of 90-98% in a humidity chamber to prevent rapid evaporation of water in the pre-polymer solution.

Irradiation of the pre-polymer solution with a simple hand-held UV lamp (365 nm) triggers photo-induced radical polymerization, thereby producing highly uniform CS-PAAm microparticles with reliable replication of 2D shapes. The microparticles thus produced can have a coefficient of variation value of 1%.

The above-described fabrication method results in stable incorporation of chitosan with retained chemical reactivity for further chemical conjugation via an acyl or nucleophilic substitution reaction. Advantages of the method include eliminating the requirement of delicate microflow control and expensive equipment, allowing use of slow-polymerizing monomers such as acrylamide in a simple and readily scalable manner, and expanding monomer's choices for fabrication.

It is noteworthy that formation of consistent and highly tunable macroporous structures can be achieved by simply adding a low content of a poly(ethylene glycol) (PEG) porogen into the aqueous pre-polymer solution. Typically, the poly(ethylene glycol) porogen has a molecular weight of 200 to 20,000 Da (e.g., 1,000 to 15,000 Da and 5,000 to 10,000 Da) and a content of 1-4 w/v %.

Further covered by this invention is a polymeric hydrogel microparticle that contains polyacrylamide and chitosan, in which the chitosan is uniformly incorporated in a polyacrylamide matrix. The microparticle has a coefficient variation of 0 to 2% (e.g., 1%) and contains macropores having an average size of 1 to 60 nm (e.g., 11 to 60 nm).

Fluorescent labeling studies that use an amine-reactive N-hydroxyl succinimidyl (NHS) ester form of fluorescein demonstrate chitosan's retained chemical reactivity and its highly uniform and highly stable incorporation in the polymeric hydrogel microparticle.

Further, as set forth above, the macroporous hydrogel microparticle prepared using the method of this invention is capable of transporting biomolecules conjugated to it. Typically, the microparticle is capable of conjugating to a biomolecule that has a molecular weight greater than 120,000 Da (preferably, greater than 200,000 Da, e.g., 240,000 Da) and reaching conjugation completion within 8 hours (e.g., within 1 hour; see EXAMPLE 5 below). The microparticle can have a total polymer content of 5 to 50 w/v % (e.g., 5 to 25 w/v % and 10 to 20 w/v %).

Moreover, protein conjugation studies that use red florescent protein R-phycoerythrin (R-PE) indicate tunable macroporous structures in the microparticle, resulting from addition of a 1-4 w/v % content of PEG for enhanced protein conjugation capacity. The protein conjugation can proceed via a rapid biorthogonal tetrazine-trans-cyclooctene (Tz-TCO) ligation reaction with minimal nonspecific binding.

Finally, studies of protein conjugation kinetics show that the microparticles are capable of rapidly conjugating to biomolecules having MW greater than 120,000 Da (e.g., greater than 200,000 Da) and reaching complete penetration and conjugation within 8 hours (e.g., within 1 hour).

The microparticle can be used in various biomedical applications including, among others, biosensing, medical diagnosis, and delivery of therapeutic agents.

Also within the scope of this invention is a one-pot method of conjugating biomolecules with polymeric hydrogel microparticles.

In this one-pot method, two bioorthogonal click reactions, i.e., a strain-promoted alkyne-azide cycloaddition (SPAAC) reaction and a Tz-TCO ligation reaction, take place. Via these two bioorthogonal click reactions, 2D shape-encoded polymeric hydrogel microparticles conjugate to biomolecules, e.g., single-stranded DNA and R-PE, to produce microparticle-biomolecule conjugates with high selectivity and minimal nonspecific binding.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. The publication cited herein is incorporated by reference.

Described below are materials used in EXAMPLE 1 for preparing polymeric hydrogel microparticles and in EXAMPLES 2-6 for evaluating the microparticles.

Chitosan oligosaccharide lactate (CS, average $M_n$ 5,000 Da, >90% deacetylation), acrylamide, bisacrylamide (Bis), poly(ethylene glycol) (PEG, average MW 8,000 Da), 2-hydroxy-2-methylpropiophenone (photoinitiator, PI), and saline sodium citrate (SSC) buffer (20× concentrate, molecular biology grade) were purchased from Sigma-Aldrich (St. Louis, Mo.). 5-(and 6-)carboxyfluorescein succinimidyl ester (NHS-fluorescein) was purchased from Pierce Biotechnology (Rockford, Ill.). Tetrazine (Tz)-$PEG_5$-NHS ester, azadibenzocyclooctyne (ADIBO)-sulfo-NHS ester, and trans-cyclooctene (TCO)-$PEG_4$-NHS ester were purchased from Click Chemistry Tools (Scottsdale, Ariz.). Tween 20 (TW20) and poly(dimethylsiloxane) (PDMS) elastomer kits (Sylgard 184, Dow Corning, Auburn, Mich.) were purchased from Thermo Fisher Scientific. Single-stranded (ss) DNA was purchased from Integrated DNA Technologies (Coralville, Iowa); azide-terminated and fluorescently labeled ssDNA (F-DNA-azide, 5'-/azide/ATGAT-GATGATGATGATG/FAM/-3'). Red fluorescent protein R-Phycoerythrin (R-PE in sodium phosphate buffer, pH 7.0 with ammonium sulfate) was purchased from AnaSpec (Fremont, Calif.). All of the reagents were analytical grade and used without further purification unless noted otherwise.

Described below are imaging methods used in EXAMPLES 2-6.

Chitosan-polyacrylamide (CS-PAAm) hydrogel microparticles were visualized with an Olympus BX51 epifluorescence microscope using standard green (U-N31001) and red (U-N31002) filter sets (Chroma Technology Corp., Rockingham, Vt.) for green fluorescent molecules (fluorescein and F-DNA) and R-PEs respectively, and fluorescence micrographs were captured with a DP70 digital microscope camera. Fluorescence intensity was evaluated with ImageJ software (http://imagej.nih.gov/ij/). Confocal micrographs were acquired on a Leica DMIRE2 microscope (Wetzlar, Germany) The particles were analyzed with a 20× objective (0.7 NA) at 488 nm and 543 nm excitation for the green fluorescent molecules and the R-PEs respectively, and the depth scan increment was 1 µm.

Example 1

Fabrication of CS-PAAm Hydrogel Microparticles

CS-PAAm hydrogel microparticles were fabricated via a micromolding-based approach following the procedure described below.

An aqueous pre-polymer solution was prepared to have the following composition: 0.5% (w/v) chitosan oligomer, 15% (w/v) acrylamide and bisacrylamide (AAm:Bis=29:1), and 2% (v/v) PI, with or without a 1-4% long-chain poly (ethylene glycol) (LC PEG) porogen (MW 8,000 Da). The chitosan oligomer was dissolved in de-ionized water and mixed directly with the other components to form the aqueous pre-polymer solution. The pre-polymer solution was placed into a PDMS micromold (1600 wells per a mold), which was formed with Sylgard 184 following overnight incubation at 65° C. on a silicon master mold fabricated by standard photolithography, as reported in Jung et al., Langmuir, 2012, 28, 17061-17070. Upon the addition of the pre-polymer solution into the micromold, air bubbles in the microwells were removed by rubbing the mold with a disposable plastic pipet tip. The excess pre-polymer solution was simply taken away by pipetting, and then the filled mold was sealed with a PDMS-coated glass slide except for the square region of the microwells (roughly 0.7 cm×0.7 cm) to make a small gap between the glass surface and the top portion of the microwells. To prevent rapid evaporation of the preparticle solution, the procedures above were carried out in a humidity chamber with approximately 92% relative humidity. The sealed mold was then placed on an aluminum mirror (Thorlabs, Newton, N.J.) and exposed to 365 nm UV light with an 8 W hand-held UV lamp (Spectronics Corp., Westbury, N.Y.) for 1 hour to form polymeric hydrogel microparticles. The microparticles thus formed were released from the microwells by physically bending the mold, and then water containing 0.5% (v/v) TW20 was placed on the top of the mold to collect the particles by pipetting. The microparticles were then transferred to a microcentrifuge tube and rinsed to remove any unreacted chemicals as follows: mixing the particles in 5×SSC buffer solution containing 0.05% (v/v) TW20 by pipetting, allowing them to settle to the tube bottom, and removing the supernatant. The rinsing step was repeated at least 5 times.

For comparative studies, polyacrylamide (PAAm) microparticles without chitosan were fabricated in the same manner as described above under the following conditions: pre-solutions containing 15% (w/v) acrylamide solution, 2% (v/v) Darocur 1173 (photo initiator), and LC PEG porogen (MW 8,000 Da, 0-4 w/v %). These pre-polymer solutions were added to hexagon-shaped PDMS molds and photopolymerized under UV light (365 nm) to form various PAAm microparticles without chitosan.

Example 2

Fluorescent Labeling Studies of Microparticles with and without Chitosan

Fluorescent labeling studies of microparticles with and without chitosan were conducted following the procedure described below.

Fluorescent Labeling of the Microparticles with Chitosan

For fluorescent labeling, the CS-PAAm microparticles (roughly 1000 particles) prepared in EXAMPLE 1 were incubated in 5×SSC buffer solution containing 0.05% (v/v) TW20 with 0.5 mM NHS-fluorescein for 1 hour on a rotator at room temperature covered with aluminum foil to minimize exposure to light. The unreacted NHS-fluorescein molecules were then removed by rinsing the particles 5 times using the rinsing procedure described in EXAMPLE 1.

To examine the chemical functionality of the chitosan incorporated into the microparticles, an amidation reaction was performed to react hexagon shape-based microparticles with an NHS-ester form of fluorescein (NHS-fluorescein) via a nucleophilic substitution $S_N2$ reaction. These microparticles were formed of short-chain chitosan ($M_n$ 5 kDa) and polyacrylamide (CS-PAAm) using a micromold in the presence of LC PEG porogens (MW 8 kDa) of various contents, i.e., 0 w/v %, 1 w/v %, 2 w/v %, and 4 w/v %.

Imaging was performed to collect bright-field micrographs and their corresponding fluorescence micrographs, confocal micrographs, and 3D fluorescence contour plot. Bright-field micrographs showed that the CS-PAAm microparticles were fabricated in a consistent manner with all the LC PEG porogen conditions examined, indicating the robust nature of the replica molding technique. The microparticles fabricated with 4 w/v % PEG porogen showed faint brown color, suggesting formation of macropores. The fluorescence micrographs showed that the CS-PAAm microparticles were uniformly labeled with fluorescein resulting from the $S_N2$ reaction between the chitosan primary amines and the NHS-fluorescein. Specifically, the average fluorescence intensity measured from at least 5 microparticles for each condition ranged from 38 to 51 at 0.1 s exposure time, with consistently small standard deviations for all the LC PEG porogen contents.

Notably, the fluorescence across each microparticle's area appeared highly uniform for all the conditions examined. This uniform fluorescence was further confirmed by the 3D fluorescence contour plot from one of the CS-PAAm microparticles with 4 w/v % PEG porogen, as well as by the confocal microscopy images taken at the center plane of the microparticles. These results indicated that the chitosan was incorporated throughout the microparticles in a highly uniform manner under all the fabrication conditions with varying LC PEG porogen contents examined. It was also observed that the CS-PAAm microparticles with 15 w/v % total polymer content exhibited minimal mass transfer limitation for the diffusion and conjugation of small fluorescein markers (MW 473.4 Da) regardless of the LC PEG porogen content.

The above results clearly indicate uniform incorporation and retained chemical activity of the chitosan contained in the CS-PAAm microparticles.

Fluorescent Labeling of the Microparticles without Chitosan

PAAm microparticles without chitosan prepared in EXAMPLE 1 were reacted with NHS-fluorescein for 1 hour. All imaging experiments were conducted in the same manner as described above.

Bright-field micrographs showed highly uniform hexagon-shaped PAAm microparticles prepared with various PEG contents, further confirming consistent and robust nature of the replica molding technique. The microparticles with 4 w/v % PEG porogen showed faint brown color similar to that exhibited by the CS-PAAm microparticles, suggesting the formation of macropores. The fluorescence micrographs showed that the PAAm microparticles without the chitosan produced no fluorescence under the same experimental and imaging conditions as for the CS-PAAm particles, indicating that: (1) the PAAm backbone of the microparticles had minimal nonspecific adsorption with fluorescein, (2) the uniform fluorescence for the CS-PAAm particles resulted from the specific $S_N2$ reaction between the chitosan's primary amines and the NHS-ester moiety, and (3) the NHS-fluorescein reaction served as an adequate tool to examine the presence, distribution and chemical functionality of the chitosan.

In short, the results indicate that most of the fluorescence resulted from the $S_N2$ reaction between chitosan and NHS-fluorescein with minimal nonspecific binding.

Example 3

Evaluation of Stable Incorporation and Chemical Reactivity of Chitosan in a CS-PAAm Hydrogel Microparticle A study was performed to evaluate the stable incorporation and chemical reactivity of chitosan in a CS-PAAm hydrogel microparticle following the procedure described below.

Average fluorescence intensity was compared for CS-PAAm microparticles prepared in the presence of 4 w/v % PEG (MW 8 kDa) prepared according to the procedures described in EXAMPLE 1.

The fluorescence micrograph showed uniform fluorescence of the freshly prepared CS-PAAm microparticles upon labeling with NHS-fluorescein. Unexpectedly, after being stored for two-weeks at room temperature, the microparticles labeled with NHS-fluorescein showed the fluorescence micrograph had uniform fluorescence same as that of the freshly prepared ones.

Further, imaging showed minimal decrease in the average fluorescence intensity. More specifically, average fluorescence intensity measured from at least five microparticles for each condition showed 9% and 18% decrease, as compared to that of the freshly prepared ones.

These results clearly indicate that the chitosan were incorporated with the CS-PAAm particles in a stable manner, and retained chemical reactivity for an extended period.

Example 4

Protein Conjugation via a tetrazine-trans-cyclooctene (Tz-TCO) Ligation Reaction A study was performed to evaluate the protein conjugation of CS-PAAm hydrogel microparticles following the procedures described below.

TCO-Activation of R-PEs

To activate R-PEs with TCO molecules, a buffer exchange of the R-PE solution with borate buffered saline (50 mM borate, 300 mM NaCl, pH 8.5) was conducted via centrifugal filtration at 4° C. The R-PEs (2 mg/mL) were then reacted with 20-fold molar excess of TCO-PEG$_4$-NHS ester or NHS-PEG$_{12}$-azide for 30 minutes at room temperature. Unreacted chemicals were separated from the R-PE solution via centrifugal filtration (Amicon Ultra 0.5) with PBS buffer (pH 7.4). Concentrations of the final R-PE solutions were measured by UV-vis spectrophotometry (Evolution™ 300 UV-vis Spectrophotometer, Thermo scientific, Waltham, Mass.) with the characteristic absorbance peaks and molar extinction coefficients of the R-PE ($1.96 \times 10^6$ M$^{-1}$ cm$^{-1}$ at 565 nm).

Tz-TCO Reaction for R-PE Conjugation

R-PEs were conjugated with CS-PAAm particles via a Tz-TCO cycloaddition reaction. Initially, the CS-PAAm particles were first activated with Tz molecules upon 1 h incubation with 500 µM Tz-PEG$_5$-NHS ester in 5×SSC buffer solution containing 0.05% (v/v) TW20 at room temperature, and rinsed with the washing procedures described in EXAMPLE 1. The Tz-activated CS-PAAm particles were subsequently reacted with 2 µM TCO-activated R-PEs in a 5×SSC buffer solution containing 0.05% (v/v) TW20 for 24 hours at room temperature. For a protein conjugation kinetic study, the Tz-activated CS-PAAm particles were also reacted with TCO-activated R-PEs under identical conjugation conditions for various periods. The unconjugated R-PEs were removed from the particle solutions via the rinsing procedures as described above.

Protein conjugation with the shape-encoded CS-PAAm microparticles was conducted using a red fluorescent protein R-phycoerythrin (R-PE) via a rapid Tz-TCO ligation reaction. The chitosan's primary amines were activated in triangle-shaped CS-PAAm microspheres prepared in the presence of LC PEG porogens at various concentrations with an NHS-ester form of Tz. The Tz-activated microparticles were then exposed to TCO-modified R-PE (2 µM) for 24 hours at room temperature.

Bright-field micrographs of R-PE-conjugated microparticles showed uniform particle shapes and red color for the particles with LC PEG porogen, suggesting high density R-PE conjugation. Further, the fluorescence micrographs showed stark contrast in the fluorescence intensity of the R-PE-conjugated microparticles with and without the LC PEG porogens under identical imaging conditions. More specifically, the microparticles prepared without a LC PEG porogen showed minimal fluorescence (FI=2.4), while all the other three conditions showed bright and uniform red fluorescence resulting from high density conjugation of R-PE. The average fluorescence intensity appeared to increase as the LC PEG content increased, reaching a maximum value of 70 at 4 m/v % PEG porogen content under the imaging conditions used (e.g., exposure time 5 ms). Also, uniform fluorescence among the particles for every condition was consistent with small standard deviations acquired from at least 5 particles under each condition. Notably, particles prepared with 1% and 2% LC PEG porogens showed higher fluorescence around the particle edges. This higher fluorescence is further confirmed with the confocal images taken at the center plane of the microparticles, while the epifluorescence and confocal images, respectively showed complete penetration of R-PE for the 4 m/v % PEG porogen condition. Importantly, these fluorescence results clearly indicate that simple addition of small amount of LC PEG porogens (i.e., ≤4 w/v %) in the pre-polymer solution leads to substantially larger mesh sizes in direct contrast to the particles prepared without any porogen, allowing the large R-PE proteins (MW 240 kDa, ~11 nm diameter) to diffuse in and react with the Tz-activated chitosan in the microparticles. The increasing penetration depths (PD=2.9 and 13.6 µm for 1% and 2% PEG porogen conditions respectively) combined with the trend of increasing average fluorescence further confirmed that the pore size and protein conjugation capacity were simply tuned by addition of small amounts of LC PEG porogen. By contrast, particles prepared without a LC PEG porogen showed minimal protein penetration and conjugation at total polymer content of 15 w/v % (AAm-Bis ratio of 29:1), suggesting the pore size substantially smaller than the R-PE's size.

Notably, short-chain PEG (MW 400 or 600 Da) did not lead to macropore formation even at a high (e.g., 4 m/v %) PEG content, indicating the importance of the PEG size in controlling formation of macropore structures.

In short, these results show that macroporous structures can be readily created and tuned by simple addition of a low amount of LC PEG porogens to the CS-PAAm pre-polymer solution, allowing complete penetration and conjugation of large R-PE proteins via a Tz-TCO ligation reaction.

Protein Conjugation without Tz Activation

The selective nature of the tetrazine-trans-cyclooctene (Tz-TCO) cyclization reaction was further confirmed by negative control experiments with non-Tz-activated CS-PAAm microparticles and TCO-modified R-PE's for all the LC PEG porogens tested. The CS-PAAm microparticles prepared in the presence of LC PEG porogens at varying concentrations were exposed to the TCO-modified R-PE for 24 hours without Tz activation and imaged via bright-field and fluorescence microscopy under the identical reaction and imaging conditions as described above.

Bright-field micrographs showed that triangle-shaped microparticles prepared with various PEG contents were highly uniform. Yet, these microparticles without Tz-activation, unlike the Tz-activated CS-PAAm microparticles, did not show a pink color upon exposure to R-PE proteins for 24 hour, suggesting minimal amount of R-PE proteins on the non-Tz-activated particles. The fluorescence micrographs showed minimal fluorescence under identical imaging conditions, indicating that the observed uniform fluorescence resulted from the selective conjugation via Tz-TCO reaction with minimal nonspecific binding of R-PE proteins to the CS-PAAm microparticles.

Example 5

Effects of LC PEG Porogens on the Kinetics of Protein Conjugation

A study was conducted to evaluate the effects of LC PEG porogens on the kinetics of protein conjugation following the procedure described below.

The study was carried out by assessing the protein conjugation kinetics of R-PE with the CS-PAAm microparticles in the presence of varying contents of LC PEG porogen. Disk-shaped, Tz-activated CS-PAAm microparticles were exposed to 2 µM of TCO-activated R-PE, and the average fluorescence intensity and the R-PE penetration profiles were examined at different reaction times.

Initially, a normalized fluorescence intensity plot showed rapid protein conjugation for the CS-PAAm microparticles with the highest LC PEG porogen content (4 w/v %). More specifically, fluorescence intensity reached 74% of the maximum value (i.e., reaction completion) within the first 30 minutes, and 91% within the first hour. This indicated highly macroporous structures of the CS-PAAm microparticles prepared with 4 w/v % LC PEG porogens, while also providing the highest protein conjugation capacity among the conditions examined. Further, microparticles prepared with 2 w/v % LC PEG reached maximum fluorescence within the first four hours and showed less fluorescence intensity (70%; as compared with that under the 4 w/v % LC PEG condition). Moreover, microparticles prepared with 1 w/v % and no LC PEG took longer time (~8 hours) to reach reaction completion, producing lower fluorescence as compared to the microparticles prepared with higher LC PEG contents.

These results clearly illustrate readily tunable and macroporous structures that permit rapid diffusion and conjugation of large biomolecules by simple addition of a low content LC PEG porogen.

Notably, the protein R-PE has MW 240 kDa, which corresponds to hydrodynamic diameter of ~11 nm. Complete penetration and conjugation of R-PE within 1 hour under the 4 w/v % LC PEG condition indicates that the mesh size, i.e., the average pore size, is substantially larger than 11 nm. This demonstrates that the microparticles of this invention can be used for protein biosensing and medical diagnostics applications, as the complete conjugation of large proteins (e.g., antibodies, M.W. ~150 kDa) are achieved within a clinically relevant assay time of less than 3 hours.

The CS-PAAm microparticles of this invention unexpectedly demonstrated substantially improved conjugation kinetics, as compared with known hydrogel microparticles. More specifically, the CS-PEG microparticles prepared with 40 w/v % poly(ethylene glycol) diacrylate (PEGDA, MW 700 Da) using in a similar molding-based fabrication method did not reach completion of R-PE conjugation reaction even after 48 hours (see Jung et al., *Biomacromolecules*, 2013, 14, 3892-3902), and the CS-PEG microspheres prepared with 10 w/v % PEGDA took over 10 hours to reach conjugation completion (see Jung et al., *Chem. Mater.*, 2015, 27, 3988-3998). By contrast, the CS-PAAm microparticles of this invention reached conjugation completion within 1 hour when prepared with a 4 w/v % content of LC PEG porogen and reached conjugation completion within 8 hours when prepared without using PEG porogens. This suggests that there existed minimal mass transfer limitation of R-PE diffusion through the CS-PAAm microparticles (4 w/v % LC PEG), resulting from highly macroporous structures.

Furthermore, the trend of fluorescence intensity (i.e., protein conjugation capacity: 4 w/v % porogen>2 w/v % porogen>1 w/v % porogen>no porogen) was found to be relatively consistent with those obtained from triangle-shaped particles, indicating reliable fabrication of macroporous microparticles with tunable porosity and retained chemical functionality.

In addition, imaging was conducted to examine the cross-sectional fluorescence profiles and penetration depths (PD) of the R-PE-conjugated microparticles at different conjugation times via confocal microscopy at the particles' center plane. It was observed that near-complete penetration of R-PE at 0.5 hour for the microparticles prepared with 4 w/v % LC PEG porogen, illustrating a macroporous nature. The confocal images of the microparticles after this time point showed complete penetration and uniform fluorescence profile throughout the microparticle cross-section. Also, the PD of the microparticles prepared with 2 w/v % LC PEG porogen gradually increased from 6.5 to 12.6 µm over 8 hours. This trend was also observed for microparticles prepared with 1 w/v % LC PEG porogen, in which the PD increased from 3.3 to 6.5 µm. It was observed that the microparticles prepared without any LC PEG porogen showed minimal increase in the PD (0 to 3.3 µm) over 8 hour. This minimal increase and the small penetration depth of ~3 µm were similar to those observed for CS-PEG microparticles fabricated with 40 w/v % PEGDA, as reported in Jung et al., *Biomacromolecules*, 2013, 14, 3892-3902. This indicates that the pre-polymer condition, i.e., 15 w/v % total polymer content, 29:1 AAm:Bis ratio, and no LC PEG porogen, resulted in micriparticles having pore sizes substantially smaller than the R-PE's size.

Finally, relatively small error bars were observed for five microparticles under each condition for all of the R-PE-conjugated microparticles, indicating consistently uniform fabrication and rapid conjugation.

In sum, the study of the kinetics of protein conjugation clearly demonstrates that rapid protein conjugation was achieved by simply tuning of the pre-polymer solution with addition of a low content of LC PEG porogen.

Example 6

One-Pot Conjugation of Biomolecules with Polymeric Hydrogel Microparticles

A study was performed to evaluate one-pot conjugation of biomolecules with polymeric hydrogel microparticles following the procedure described below.

CS-PAAm microparticles were incubated in 5×SSC buffer solution containing 0.05% (v/v) TW20 with 500 μM ADIBO-sulfo-NHS ester for 1 h on a rotator at room temperature for activation with ADIBO. The unreacted ADIBO-sulfo-NHS ester molecules were rinsed 5 times using the rinsing procedure described in EXAMPLE 1. The ADIBO-activated microparticles were then reacted with 10 μM of azide-terminated ssDNAs (F-DNA-azide) for 24 hours at room temperature. The unconjugated DNAs were then rinsed 5 times using the rinsing procedure.

One-pot conjugation two biomolecules, i.e., single-stranded DNA (ssDNA) and R-PE, with CS-PAAm particles with different 2D shapes was performed via two bioorthogonal reactions. Namely, a strain-promoted alkyne-azide cycloaddition (SPAAC) reaction was utilized to anchor azide-modified ssDNA onto CS-PAAm particles activated with (azadibenzocyclooctyne) (ADIBO), and a Tz-TCO ligation reaction was used to anchor TCO-activated R-PE onto Tz-activated CS-PAAm particles with a different 2D shape. These two bioorthogonal reactions allowed programmable functionalization of the two biomolecules in one pot simultaneously. CS-PAAm microparticles with three distinct 2D shapes were fabricated by the molding technique described in Example 1. Upon activation of the chitosan's primary amines with ADIBO and Tz respectively, the three types of particles were mixed together and exposed to a mixture of azide-modified ssDNA with fluorescein label (green) and TCO-activated R-PE (red) in one pot. CS-PAAm particles without any activation were used as a negative control.

Overlay images showed the three types of microparticles having distinct 2D shapes. Fluorescence overlay images illustrated minimal fluorescence of the negative control microparticles, indicating a non-fouling nature, i.e., minimal nonspecific binding, of the CS-PAAm microparticles with the biomolecules (i.e., ssDNA and R-PE) and an orthogonal nature of the two reactions.

Furthermore, green and red fluorescence images showed the orthogonal conjugation of two chemically distinct biomolecules, i.e., ssDNA and R-PE, with each microparticle type via a SPAAC reaction and a Tz-TCO reaction, respectively. In other words, the ssDNA conjugation proceeded via a SPAAC reaction (green) and the R-PE conjugation proceeded via a Tz-TCO ligation reaction (red), yielding minimal cross-reactivity.

In sum, these results demonstrate simultaneous conjugation of two distinct biomolecules with different 2D shape-encoded CS-PAAm microparticles in an orthogonal, one-pot manner.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A polymeric hydrogel microparticle comprising polyacrylamide and chitosan, the chitosan uniformly incorporated in a polyacrylamide matrix, wherein the microparticle has a coefficient of variation of 0 to 2% and contains macropores having an average size of 1 to 60 nm, wherein the chitosan has an average molar mass of 4,500-200,000 Da and the chitosan contains primary amines each having a pKa value of 6.0-6.9.

2. The polymeric hydrogel microparticle of claim 1, wherein the microparticle has a total polymer content of 5 to 50 w/v %.

3. The polymeric hydrogel microparticle of claim 1, wherein the microparticle is capable of conjugating to a biomolecule that has a molecular weight greater than 120,000 Da.

4. The polymeric hydrogel microparticle of claim 3, wherein the biomolecule has a molecular weight greater than 200,000 Da.

5. The polymeric hydrogel microparticle of claim 4, wherein the biomolecule has a molecular weight of 240,000 Da.

6. The polymeric hydrogel microparticle of claim 5, wherein the microparticle has a total polymer content of 5 to 50 w/v % and is capable of conjugating to a biomolecule that has a molecular weight greater than 200,000 Da.

7. The polymeric hydrogel microparticle of claim 1, wherein the macropores have an average size greater than of 11 nm to 60 nm.

8. The polymeric hydrogel microparticle of claim 7, wherein the microparticle is capable of conjugating to a biomolecule that has a molecular weight greater than 120,000 Da.

9. The polymeric hydrogel microparticle of claim 8, wherein the biomolecule has a molecular weight greater than 200,000 Da.

10. The polymeric hydrogel microparticle of claim 9, wherein the biomolecule has a molecular weight of 240,000 Da.

11. The polymeric hydrogel microparticle of claim 1, wherein the microparticle has a 2D shape.

12. The polymeric hydrogel microparticle of claim 11, wherein the 2D shape is hexagon, triangle, square, disk, pentagon, or cross.

* * * * *